(12) United States Patent
Buechler et al.

(10) Patent No.: US 6,803,040 B1
(45) Date of Patent: *Oct. 12, 2004

(54) DERIVATIVES OF TRICYCLIC ANTIDEPRESSANTS AND PROTEIN AND POLYPEPTIDE TRICYCLIC ANTIDEPRESSANT DERIVATIVE CONJUGATES AND LABELS

(75) Inventors: Kenneth Francis Buechler, San Diego, CA (US); Joseph Barry Noar, Solana Beach, CA (US)

(73) Assignee: Biosite, Inc., San Diego, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1443 days.

(21) Appl. No.: 08/517,949

(22) Filed: Aug. 22, 1995

(51) Int. Cl.$^7$ ............................................. A61K 39/385
(52) U.S. Cl. ..................... 424/194.1; 436/501; 436/518; 436/543; 530/403; 530/388.9; 530/398.8; 435/7.1; 435/7.9
(58) Field of Search .................. 435/7.1, 7.9; 436/591, 436/518, 536, 543, 547, 822, 501; 530/403, 388.9, 389.8, 398.8; 424/194.1

(56) References Cited

U.S. PATENT DOCUMENTS

| | | | |
|---|---|---|---|
| 4,067,774 A | | 1/1978 | Rubenstein et al. ......... 435/188 |
| 4,223,013 A | | 9/1980 | Hu et al. .................. 530/398.8 |
| 4,275,160 A | | 6/1981 | Singh et al. .............. 530/398.8 |
| 4,307,245 A | | 12/1981 | Hu et al. ..................... 562/442 |
| 4,495,281 A | * | 1/1985 | Buckler et al. ................. 435/7 |
| 4,629,691 A | | 12/1986 | Collins et al. ................ 435/7.9 |
| 4,772,697 A | * | 9/1988 | Collins et al. ............... 540/591 |
| 4,952,336 A | | 8/1990 | Brynes et al. .......... 252/301.16 |
| 5,028,535 A | | 7/1991 | Buechler et al. .............. 435/7.1 |
| 5,089,391 A | | 2/1992 | Buechler et al. .............. 435/7.1 |
| 5,302,703 A | * | 4/1994 | Buechler et al. ............. 530/404 |
| 5,302,715 A | * | 4/1994 | Buechler et al. ............. 540/507 |
| 5,331,109 A | * | 7/1994 | Buechler ..................... 530/404 |

FOREIGN PATENT DOCUMENTS

| | | |
|---|---|---|
| EP | 0167256 | 1/1986 |
| EP | 0226730 | 7/1987 |
| WO | 9411405 | 5/1994 |

OTHER PUBLICATIONS

Liu et al., "Production and Characterization of High Affinity MOnoclonal Antibodies to Cyclic Anti–Depressant Molecules", Clin. Toxicol. 25 (7), 527–538 (1987).*
Virtanen, Scand. J. Clin. Lab. Invest. 40, 191–197 (1980).*
Hoffsommer et al., "The Homoallylic Rearrangement in the Synthesis of Amitriptyline and Related Systems," *J. Org. Chem.* 27(12):4134–4137 (1963).

* cited by examiner

*Primary Examiner*—Donna C. Wortman
(74) *Attorney, Agent, or Firm*—Foley & Lardner LLP

(57) ABSTRACT

The present invention is directed to novel tricyclic antidepressant derivatives which are synthesized for the covalent attachment to antigens (proteins or polypeptides) for the preparation of antibodies or receptors to tricyclic antidepressant and tricyclic antidepressant metabolites. The resulting novel antigens may be used for the production of antibodies or receptors using standard methods. Once generated, the antibodies or receptors and the novel derivatives which are covalently attached to proteins, polypeptides or labels may be used in the immunoassay process.

25 Claims, 2 Drawing Sheets

DERIVATIVES OF TRICYCLIC ANTIDEPRESSANTS AND PROTEIN AND POLYPEPTIDE TRICYCLIC ANTIDEPRESSANT DERIVATIVE CONJUGATES AND LABELS

FIELD OF THE INVENTION

This invention is in the field of ligand receptor assays, including immunoassays, for the detection of tricyclic antidepressants and selected metabolites of tricyclic antidepressants in a fluid sample. More particularly, this invention relates to methods for the synthesis of novel tricyclic antidepressant derivatives and protein and polypeptide tricyclic antidepressant derivative conjugates and labels for use in the preparation of antibodies to tricyclic antidepressant metabolites and for use in the immunoassay process.

BACKGROUND OF THE INVENTION

Tricyclic antidepressants have been used to treat endogenous depression since 1957. The therapeutic dose of tricyclic antidepressants varies from person to person and to achieve an effective dose for a patient, a simple and accurate methodology is required for the measurement of tricyclic antidepressants and their metabolites in blood and urine. In addition, doses of tricyclic antidepressants above the therapeutic amount can cause toxic side effects and death. Thus, a medical need exists for antibodies and diagnostics to rapidly detect tricyclic antidepressants and tricyclic antidepressant metabolites in order to monitor tricyclic antidepressant therapy and treat tricyclic antidepressant overdose.

The preparation of antibodies to tricyclic antidepressants and tricyclic antidepressant metabolites requires the synthesis of tricyclic antidepressant derivatives in order to covalently attach the derivative to an antigenic polypeptide or protein. In addition, the tricyclic antidepressant derivative is covalently attached to various polypeptides, proteins or labels for use in screening antibodies and in the immunoassay process. The tricyclic antidepressant derivative should mimic the structure of the tricyclic antidepressant metabolites sought to be measured. Therefore, the selection and synthesis of the types of tricyclic antidepressant derivatives for covalent attachment to proteins, polypeptides or labels are critical. In addition, the tricyclic antidepressant derivatives need to be stable and soluble in an aqueous solution.

Tricyclic antidepressant compounds and conjugates for immunization and immunoassay have been described in U.S. Pat. Nos. 4,223,013, 4,275,160, 4,307,245, 4,629,691 and 4,772,697 and a European Patent Application No. 86113654.7.

SUMMARY OF THE INVENTION

The present invention is directed to novel tricyclic antidepressant derivatives which are synthesized for the covalent attachment to antigens (proteins or polypeptides) for the preparation of antibodies to tricyclic antidepressants and tricyclic antidepressant metabolites. The resulting novel antigens may be used for the production of antibodies using standard methods. Once generated, the antibodies and the novel derivatives which are covalently attached to proteins, polypeptides or labels may be used in the immunoassay process.

DEFINITIONS

In accordance with the present invention and as used herein, the following terms, are defined with the following meanings, unless explicitly stated otherwise.

"Drug" shall mean any compound or ligand which either as a result of spontaneous chemical reaction or by enzyme catalyzed or metabolic reaction, generates an intrinsic activity when administered to a biological system. The drug may be metabolized to a derivative of the drug by a biological system. Common examples of drugs and their metabolites are tricyclic antidepressants, morphine, barbiturates, tetrahydrocannabinol, phencyclidine, amphetamines, methamphetamines, opiates, benzodiazepines, cocaine, estrone-3-glucuronide, pregnanediol-glucuronide, cotinine, lysergic acid diethylamide, methadone, propoxyphene, anabolic steroids.

"Drug derivative" shall mean a ligand derivative, drug, drug metabolite or a drug analogue conjugated to a linking group.

"Drug metabolite" shall mean a compound upstream or downstream from a drug in a biochemical or metabolic pathway, or an intermediate.

"Label" shall mean a signal development element or a means capable of generating a signal, for example, a dye or an enzyme. The attachment of a drug derivative to the label can be through covalent bonds, adsorption processes, hydrophobic and/or electrostatic bonds, as in chelates and the like, or combinations of these bonds and interactions.

"Binding domain" shall refer to the molecular structure associated with that portion of a receptor that binds ligand. More particularly, the binding domain may refer to a polypeptide, natural or synthetic, or nucleic acid encoding such a polypeptide, whose amino acid sequence represents a specific region of a protein, said domain, either alone or in combination with other domains, exhibiting binding characteristics which are the same or similar to those of a desired ligand/receptor binding pair. Neither the specific sequences nor the specific boundaries of such domains are critical, so long as binding activity is exhibited. Likewise, used in this context, binding characteristics necessarily includes a range of affinities, avidities and specificities, and combinations thereof, so long as binding activity is exhibited.

"Linking group" shall mean the "chemical arm" between the protein, polypeptide or label and a drug or drug derivative. As one skilled in the art will recognize, to accomplish the requisite chemical structure, each of the reactants must contain the necessary reactive groups. Representative combinations of such groups are amino with carboxyl to form amide linkages, or carboxy with hydroxy to form ester linkages or amino with alkyl halides to form alkylamino linkages, or thiols with thiols to form disulfides, or thiols with maleimides or alkylhalides to form thioethers. Obviously, hydroxyl, carboxyl, amino and other functionalities, where not present may be introduced by known methods. Likewise, as those skilled in the art will recognize, a wide variety of linking groups may be employed. The structure of the linkage should be a stable covalent linkage formed to attach the drug or drug derivative to the protein, polypeptide or label. In some cases the linking group may be designed to be either hydrophilic or hydrophobic in order to enhance the desired binding characteristics of the ligand and the receptor. The covalent linkages should be stable relative to the solution conditions under which the ligand and linking group are subjected. Generally preferred linking groups will be from 1–20 carbons and 0–10 heteroatoms (NH, O, S) and may be branched or straight chain. Without limiting the foregoing, it should be obvious to one skilled in the art that only combinations of atoms which are chemically compatible comprise the linking group. For example, amide, ester, thioether, thioester, keto, hydroxyl, carboxyl, ether groups in combinations with carbon-carbon bonds are acceptable examples of chemically compatible linking groups. Other chemically compatible compounds which may comprise the linking group are set forth in this Definition section and hereby are incorporated by reference.

"Hydrocarbyl" shall refer to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. It may refer to straight-chain, branched-chain cyclic structures or combinations thereof.

"Aryl" shall refer to aromatic groups which have at least one ring having a conjugated pi electron system and includes carbocyclic aryl, heterocyclic aryl and biaryl groups, all of which may be optionally substituted.

"Carbocyclic aryl groups" shall refer to groups wherein the ring atoms on the aromatic ring are carbon atoms. Carbocyclic aryl groups include monocyclic carbocyclic aryl groups and optionally substituted naphthyl groups.

"Monocyclic carbocyclic aryl" shall refer to optionally substituted phenyl, being preferably phenyl or phenyl substituted by one to three substituents, such being advantageously lower alkyl, hydroxy, lower alkoxy, lower alkanoyloxy, halogen, cyano, trihalomethyl, lower acylamino, lower amino or lower alkoxycarbonyl.

"Optionally substituted naphthyl" shall refer to 1- or 2-naphthyl or 1- or 2-naphthyl preferably substituted by lower alkyl, lower alkoxy or halogen.

"Heterocyclic aryl groups" shall refer to groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl, and the like, all optionally substituted.

"Optionally substituted furanyl" shall refer to 2- or 3-furanyl or 2- or 3-furanyl preferably substituted by lower alkyl or halogen.

"Optionally substituted pyridyl" shall refer to 2-, 3- or 4-pyridyl or 2-, 3- or 4-pyridyl preferably substituted by lower alkyl or halogen.

"Optionally substituted thienyl" shall refer to 2- or 3-thienyl, or 2- or 3-thienyl preferably substituted by lower alkyl or halogen.

"Biaryl" shall refer to phenyl substituted by carbocyclic aryl or heterocyclic aryl as defined herein, ortho, meta or para to the point of attachment of the phenyl ring, advantageously para; biaryl is also represented as the —C$_6$H$_4$—Ar substituent where Ar is aryl.

"Aralkyl" shall refer to an alkyl group substituted with an aryl group. Suitable aralkyl groups include benzyl, picolyl, and the like, and may be optionally substituted.

"Lower" referred to herein in connection with organic radicals or compounds respectively defines such with up to and including 7, preferably up to and including 4 and advantageously one or two carbon atoms. Such groups may be straight chain or branched.

The terms (a) "alkyl amino," (b) "arylamino," and (c) "aralkylamino," respectively, shall refer to the groups —NRR' wherein respectively, (a) R is alkyl and R' is hydrogen or alkyl; (b) R is aryl and R' is hydrogen or aryl, and (c) R is aralkyl and R' is hydrogen or aralkyl.

The term "acyl" shall refer to hydrocarbyl-CO— or HCO—.

The terms "acylamino" refers to (RCONCR)— and (RCO$_2$N)— respectively, wherein each R is independently hydrogen or hydrocarbyl.

The term "hydrocarbyloxycarbonylmethyl" shall refer to the group ROC(O)O— wherein R is hydrocarbyl.

The term "lower carboalkoxymethyl" or "lower "hydrocarbyloxycarbonylmethyl" refers to hydrocarbyl-OC(O)CH$_2$— with the hydrocarbyl group containing ten or less carbon atoms.

The term "carbonyl" refers to —C(O)—.

The term "carboxamide" or "carboxamido" refers to —CONR$_2$ wherein each R is independently hydrogen or hydrocarbyl.

The term "lower hydrocarbyl" refers to any hydrocarbyl group of ten or less carbon atoms.

The term "alkyl" refers to saturated aliphatic groups including straight-chain, branched chain and cyclic groups.

The term "alkenyl" refers to unsaturated hydrocarbyl groups which contain at least one carbon-carbon double bond and includes straight-chain, branched-chain and cyclic groups.

The term "alkynyl" refers to unsaturated hydrocarbyl groups which contain at least one carbon-carbon triple bond and includes straight-chain, branched-chain and cyclic groups.

The term "hydrocarbyloxycarbonylamino" refers to a urethane, hydrocarbyl-O—CONR— wherein R is H or hydrocarbyl and wherein each hydrocarbyl is independently selected.

The term "di(hydrocarbyloxycarbonyl)amino" refers to (hydrocarbyl-O—CO)$_2$N— wherein each hydrocarbyl is independently selected.

The term "hydrocarbylamino" refers to —NRR' wherein R is hydrocarbyl and R' is independently selected hydrocarbyl or hydrogen.

The term "mercapto" refers to SH or a tautomeric form.

The term "methene" refers to

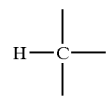

The term "methylene" refers to —CH$_2$—.

The term "alkylene" refers to a divalent straight chain or branched chain saturated aliphatic radical.

The term "oxy" refers to —O— (oxygen).

The term "thio" refers to —S— (sulfur).

"Disulfide" refers to —S—S—.

"Thioester" refers to

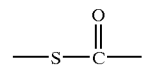

"Thioether" refers to C—S—C.

"Ester" refers to

"Analyte" shall mean substance of natural or synthetic origin sought to be detected and/or measured, said substance having a specific binding partner capable of a specific interaction with said analyte.

"Ligand" shall mean a binding partner to a ligand receptor. A substance which, if detected may be used to infer the presence of an analyte in a sample, including, without limitation, haptens, hormones, antigens, antibodies, deoxyribonucleic acid (DNA), ribonucleic acid (RNA), metabolites of the aforementioned materials and other substances of either natural or synthetic origin which may be of diagnostic interest and have a specific binding partner therefor, i.e., the ligand receptor of a ligand-receptor assay.

"Receptor" shall mean a receptor capable of binding ligand, typically an antibody, or a fragment thereof, but which may be another ligand, depending on assay design.

"Ligand-Receptor Assay" shall mean an assay for an analyte which may be detected by the formation of a complex between a ligand and a ligand receptor which is capable of a specific interaction with that ligand. Ligand-Receptor assays may be competitive or non-competitive, homogeneous or heterogeneous.

"Immunogen" shall mean a chemical or biochemical structure, determinant, antigen or portion thereof, which elicits an immune response, including, for example, polylysine, bovine serum albumin and keyhole limpid hemocyanin (KLH).

"Antigenic" shall mean a chemical or biochemical structure, determinant, antigen or portion thereof which is capable of inducing the formation of an antibody.

DETAILED DESCRIPTION OF THE PREFERRED EMBODIMENTS

Figure 1:
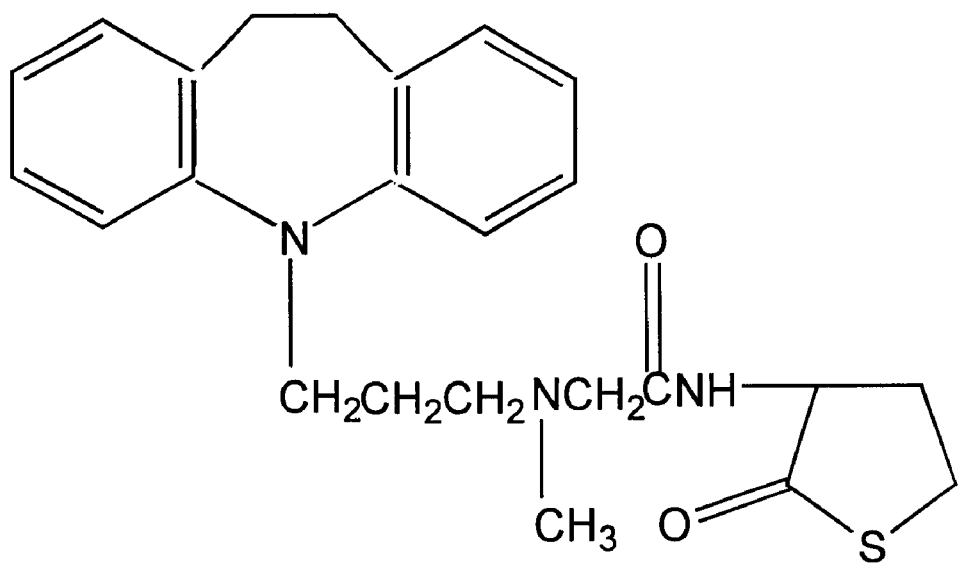
FIGS. 1–4 depict the structures of Examples 1–4, respectively.
Figure 2:
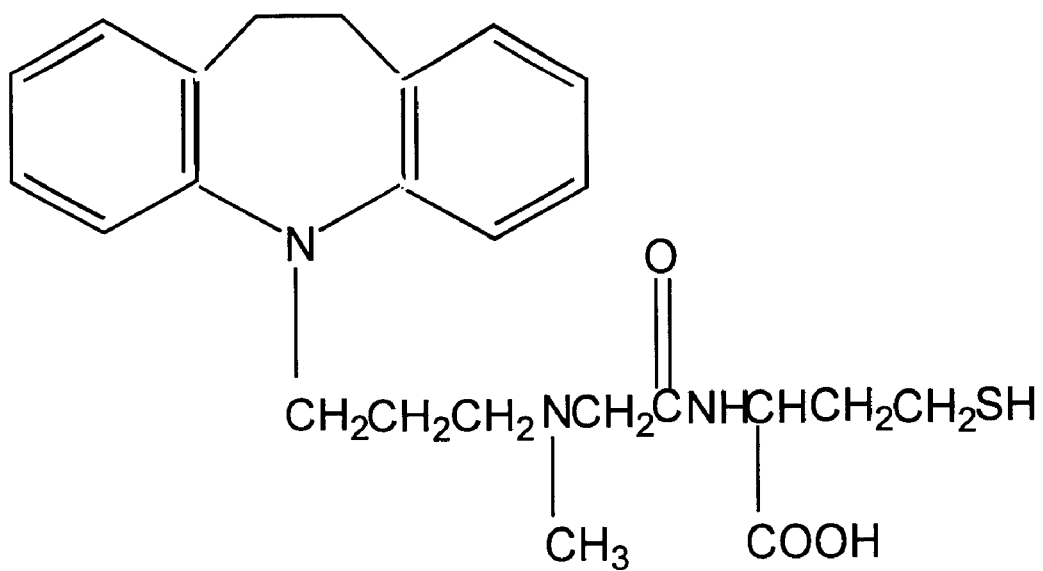
Figure 3:
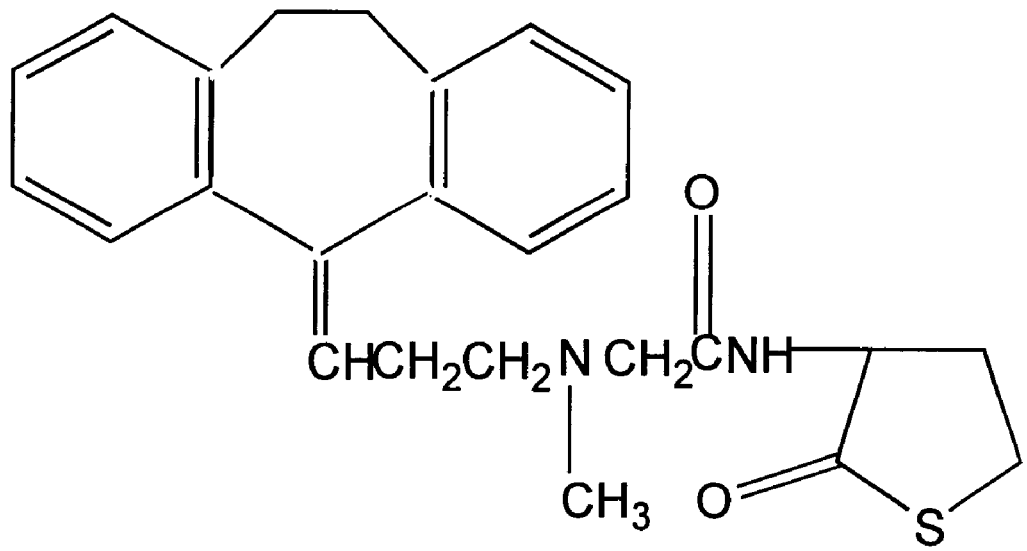
Figure 4:
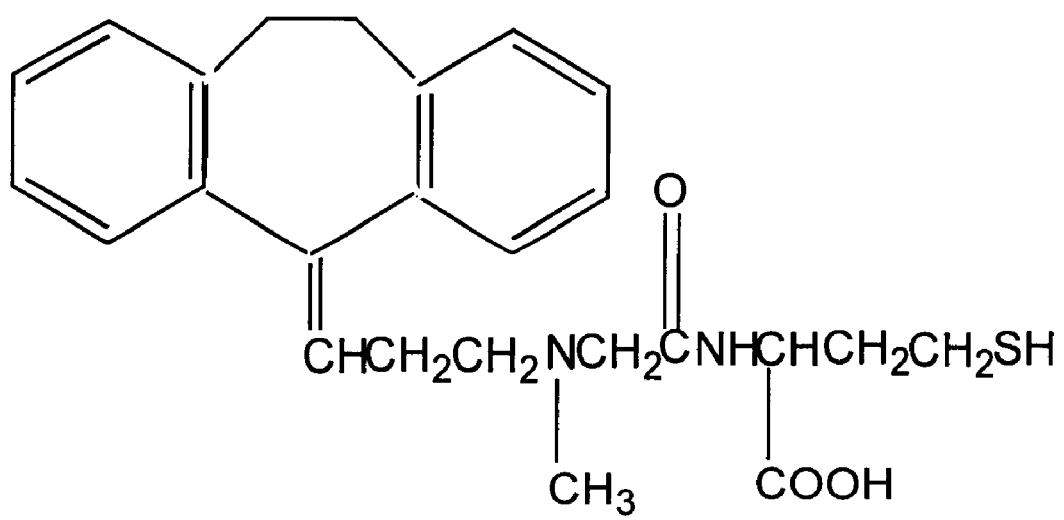

Novel compounds are described which are used in the generation of antibodies and in the immunoassay process generally. The compounds are derivatives of tricyclic antidepressants and tricyclic antidepressant metabolites. The elaboration of the alkyl chain of the tricyclic antidepressant can be performed at the aliphatic nitrogen and can include introduction of an amine, carboxylic acid or thiol function to aid in the attachment of the derivative to the protein, polypeptide or label. In addition, iminodibenzyl can be alkylated or acylated, for example, with a haloalkyl thioester or a carboxylic acid thioester, respectively, to form derivatives which can be attached to proteins, polypeptides or labels via the thiol function.

The synthesis of a particular derivative should allow for the character of the tricyclic antidepressant or tricyclic antidepressant metabolite derivative to be properly presented to the antibody or receptor in a manner which allows for the desired binding interaction. The synthesis of the linking group between the protein, polypeptide or label and the tricyclic antidepressant or tricyclic antidepressant metabolite derivative is designed to achieve the desired binding of the drug derivative and the receptor. For example, the derivative may be displaced from the surface of the protein, polypeptide or label to allow the derivative to present itself to the binding domain of receptors.

In general, the compounds of this invention have the

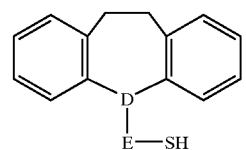

where D is C or N;

where E is a saturated or unsaturated linking group from 1–20 carbons and 0 to 10 heteroatoms (HN, O, S) either branched or in a straight chain.

In addition, the general form of the immunogenic protein or peptide molecule or label which is derivatized via an amide, disulfide, thioether, or ester bond to the molecule or label also to a compound of the formula, is of the following:

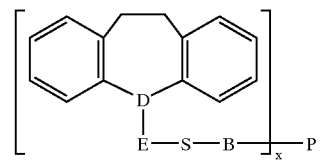

where P is an antigenic protein or polypeptide or a protein, polypeptide or label;

where x is at least one and not greater than 100;

where D is C or N;

where E is a saturated or unsaturated linking group of from 1 to 20 carbons and 0 to 10 heteroatoms (HN, O, S) either branched or straight chain;

where B is a linking group ultimately attached to a protein, polypeptide or label selected from the group comprising:

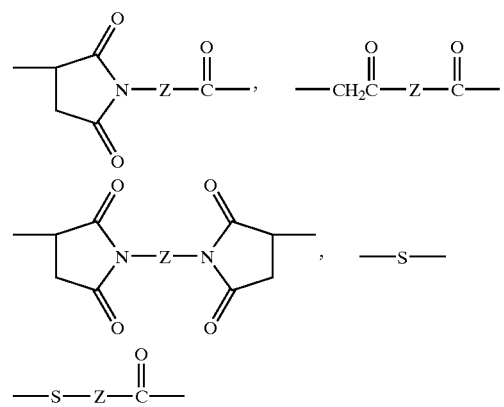

where Z is a linking group of from 1 to 20 carbons and 0 to 10 heteroatoms (NH, O, S) and may be branched or straight chain.

In general, the compounds of this invention also have the following formula:

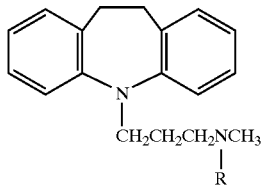

Where R is a linking group comprising one of the following

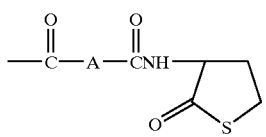

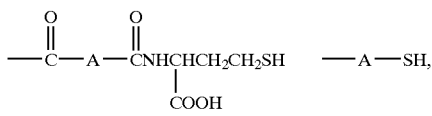

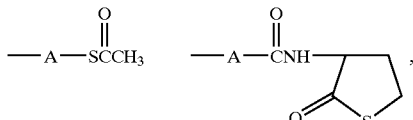

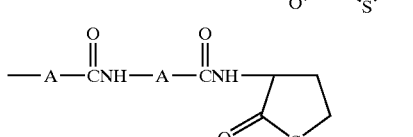

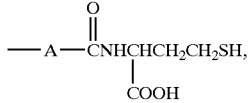

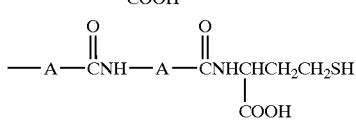

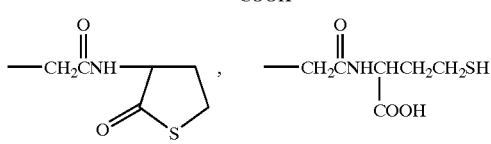

where A is a linking group of from 1 to 20 carbons and from 0 to 10 heteroatoms (NH, O, S), either branched or straight chain.

In addition, the general form of the immunogenic protein or polypeptide molecule or the protein or polypeptide molecule or label which is derivatized via an amide, disulfide, thioether, or ester bond to the molecule or label also to a compound of the formula, is of the following:

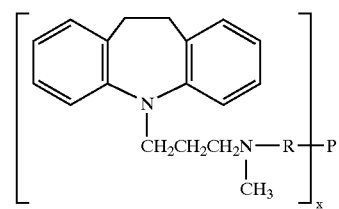

Where P is an antigenic protein or polypeptide or a protein, polypeptide or label;

where x is at least one and not greater than 100;

where R is a linking group comprising one of the following:

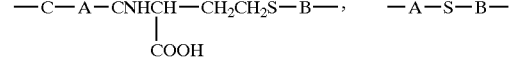

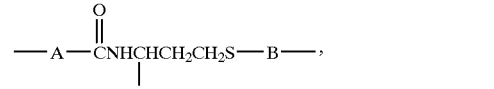

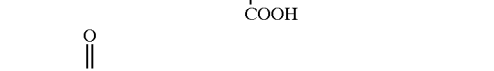

where A is a linking group of from 1 to 20 carbons and 0 to 10 heteroatoms (NH, O, S), either branched or straight chain;

where B is a linking group ultimately attached to a protein, polypeptide or label selected from the group consisting of:

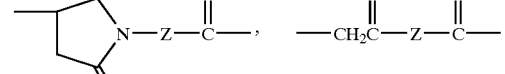

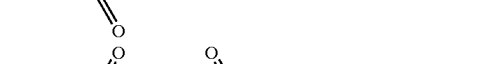

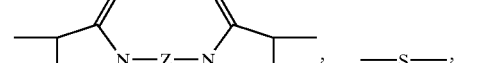

where Z is a linking group of from 1 to 20 carbons and 0 to 10 heterocarbons (NH, O, S) and may be branched or straight chain.

In general, the compounds of this invention also have the following formula:

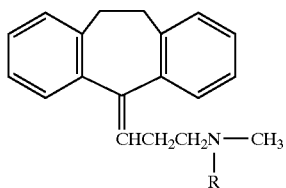

where R is a saturated or unsaturated linking group comprising one of the following:

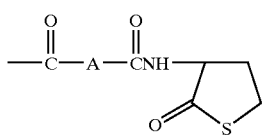

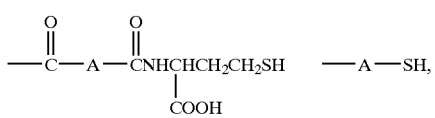

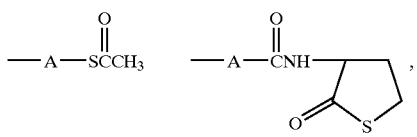

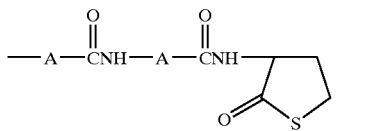

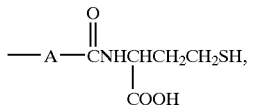

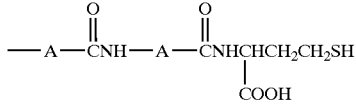

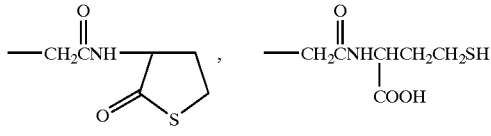

where A is a linking group of from 1 to 20 carbons and from 0 to 10 heterocarbons (NH, O, S), either branched or straight chain.

In addition, the general form of the immunogenic protein or polypeptide molecule or the protein or polypeptide molecule or label which is derivative via an amide, disulfide, thioether, or ester bond to the molecule or label also to a compound of the formula is of the following:

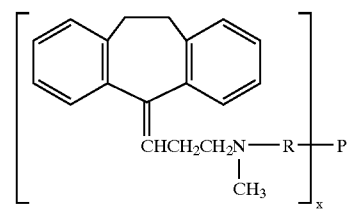

Where P is an antigenic protein or polypeptide or a protein, polypeptide or label;

Where x is at least one and not greater than 100;

Where R is a linking group comprising one of the following:

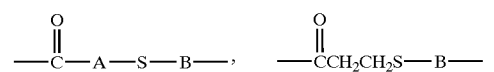

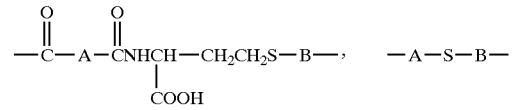

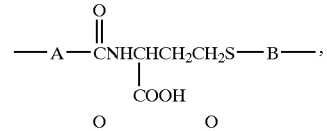

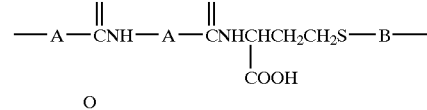

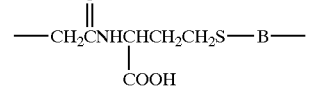

Where A is a linking group of from 1 to 20 carbons and 0 to 10 heterocarbons (NH, O, S), either branched or straight chain;

Where B is a linking group ultimately attached to a protein, polypeptide, or label selected from the group comprising:

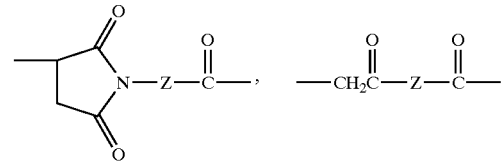

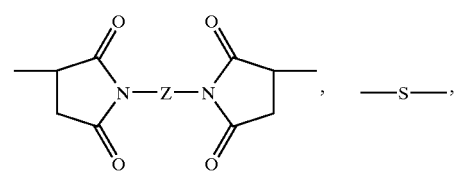

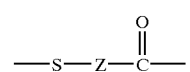

where Z is a linking group of from 1 to 20 carbons and 0 to 10 heterocarbons (NH, O, S) and may be branched or straight chain.

The preferred (best mode) compounds of this invention have the following formula:

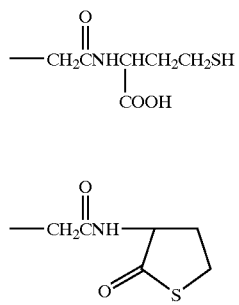

Where R is a linking group comprising one of the following:

—CH$_2$CNHCHCH$_2$SH
‖    |
O   COOH

—CH$_2$CNH—[thiolactone]
‖
O

In addition, another preferred (best mode) compounds of this invention have the following formula:

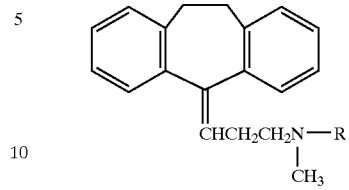

Where R is a linking group comprising one of the following:

—CH$_2$CNHCHCH$_2$CH$_2$SH
‖    |
O   COOH

—CH$_2$CNH—[thiolactone]
‖
O

In addition, the preferred (best mode) immunogenic protein or polypeptide molecule or the protein or polypeptide molecule or label derivatized via an amide or ester bond to the molecule or label to a compound of the formula is of the following:

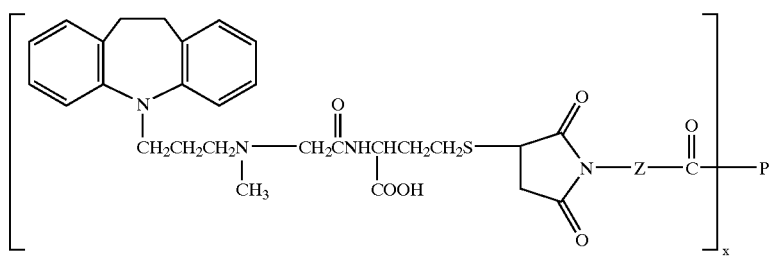

where P is an antigenic protein or polypeptide or a protein, polypeptide or label;

where x is at least one and not greater than 100;

Where Z is a linking group of from 1 to 20 carbons and 0 to 10 heterocarbons (NH, O, S) and may be branched or straight chain.

In addition, another preferred (best mode) immunogenic protein or polypeptide molecule or the protein or polypeptide molecule or label derivatized via an amide or ester bond to the molecule or label to a compound of the formula is of the following:

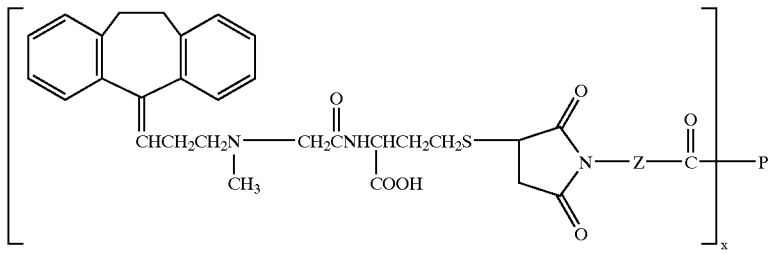

where P is an antigenic protein or polypeptide or a protein, polypeptide or label;

where x is at least one and not greater than 100;

Where Z is a linking group of from 1 to 20 carbons and 0 to 10 heterocarbons (NH, O, S) and may be branched or straight chain.

Of particular interest are tricyclic antidepressant derivatives which can be synthesized by alkylation or acylation of the secondary amine of iminodibenzyl. The alkylation reactions can be performed using various chain length alkyl halide carboxylic acids, for example, 3-iodopropionic acid or ethyl-3-iodo propionate can be reacted to form an N-alkylated carboxylic acid tricyclic antidepressant derivative, which can then be further reacted with an amino alkyl thiol ester, such as homocysteine thiolactone, to synthesize the thiol ester derivative of the tricyclic antidepressant. Acylation reactions can also be performed with iminodibenzyl using various chain length alkyl thioester carboxylic acids for example, 3-acetylthio propionic acid, to synthesize an amide thio ester derivative of tricyclic antidepressant. In addition, varying chain length derivatives of 5H-dibenzo[a,d]-10,11-dihydrocycloheptene-5-one can be synthesized having aliphatic primary or secondary amines or hydroxyl as described in J. Org. Chem. 27, 4134–4137 (1962) and the resulting unsaturated aliphatic chain can be further alkylated or acylated with haloalkyl thioesters or acids, or carboxylic acid thioesters, respectively, as described above.

Also of particular interest are tricyclic antidepressant derivatives which can be synthesized by alkylation or acylation of the secondary amine of a precursor of a nortricyclic antidepressant. The attachment of linking arms to tricyclic antidepressants, for example, desipramine, nordoxepin, nortriptyline, protriptyline, nordothiepin, norcyclobenzaprine, norclomipramine, norchlorprothixene, norchlorpromazine and amoxapine or their metabolites can be performed through derivatization of the secondary aliphatic amine. The secondary aliphatic amine may be either alkylated with various chain length alkyl halide carboxylic acids, for example, 3-iodopropionic acid, to form the N-alkylated carboxylic acid of the tricyclic antidepressant derivative, which can be further reacted with an amino alkyl thio ester, such as homocysteine thiolactone, to synthesize the thio ester derivative of the tricyclic antidepressant or acylated with various chain lengths of carboxylic acid alkyl thio esters, such as 3-acetylthiopropionic acid to form the thio ester derivative of the tricyclic antidepressant.

The thio esters of the resulting tricyclic antidepressant or tricyclic antidepressant metabolite derivatives are hydrolyzed in dilute base, for example, 0.01 M potassium hydroxide, to generate the thiol group which is reacted with the thiol reactive group, such as a maleimide, an alkyl halide or a thiol. Those skilled in the art can recognize the versatility of synthetic strategies described herein.

The compounds are synthesized as thiols or thiol esters so that their covalent attachment to proteins, polypeptides or labels can easily be performed under mild conditions, for example, pH 7 in a protein solution. The protein, polypeptide or label is reacted with a reagent which incorporates a maleimide or an alkylhalide or a thiol into the molecule. These reagents and methods for their use are available from Pierce, Rockford, Ill., for example, for incorporation of maleimide groups onto proteins, polypeptides or labels one can use succinimidyl 4-(N-maleimidomethyl)cyclohexane-1-carboxylate (SMCC), succinimidyl 4-(p-maleimidophenyl)butyrate (SMPB) or m-maleimidobenzoyl-N-hydroxysuccinimide ester (MBS). For introduction of an alkyl halide into a protein, polypeptide or label one can use N-succinimidyl(4-iodoacetyl) aminobenzoate (SIAB) also from Pierce. For introduction of a thiol group into a protein, polypeptide or label, one can use N-Succinimidyl 3-(2-pyridyldithio)-propionate (SPDP) also from Pierce. The thiol reactive group, such as maleimide, an alkyl halide or a thiol can be incorporated into the protein, polypeptide or label prior to reaction with the drug thiol but the drug thiol can also be reacted with the thiol reactive compound prior to reaction with the protein, polypeptide or label. Also, bis-maleimide compounds of varying length can be reacted with thiol containing proteins, polypeptides or labels for covalent coupling of the tricyclic antidepressant derivatives. Conversely, the bis-maleimide compound can be reacted with the thiol derivative and subsequently to the thiol containing protein, polypeptide or label.

Common bis-maleimides are bis-maleimidohexane from Pierce, N,N'-bis(3maleimidopropionyl)-2-hydroxy-1,3-propanediamine from Sigma Chemical Co., St. Louis, Mo., and 1,1'-(methylenedi-4,1-phenylene)-bismaleimide from Aldrich Chem. Co., Milwaukee, Wis. The thiol tricyclic antidepressant derivatives can also form disulfides with thiol containing polypeptide, protein or label molecules as a means to incorporate the derivative into the molecule.

The use of drug derivatives, immunogens and protein and polypeptide conjugates for generating antibodies and for use in the immunoassay process is described, for example, in U.S. Pat. Nos. 4,067,774, 4,952,336, 5,028,535 and 5,089,391.

EXPERIMENTAL EXAMPLES

Example 1

Preparation [N-(2-Butyrothiolactone)amidomethyl] desipramine

To a stirring solution of desipramine hydrochloride (303 mg, $1.0 \times 10^{-3}$ mol) and bromoacetyl-d, 1-homocysteine thiolactone (Example 5) (262 mg, $1.1 \times 10^{-3}$ mol) in anhydrous dimethylformamide (10 ml) was added freshly powered anhydrous potassium carbonate (304 mg, $2.2 \times 10^{-3}$ mol). The mixture was stirred at room temperature for 45 hours. The solvent was evaporated under vacuum, the residue treated with ethyl acetate (20 ml) and the mixture filtered. The filtrate was acidified to pH 2 by dropwise addition of a 1 N solution of hydrogen chloride in diethyl ether (2 ml) to precipitate the crude product hydrochloride. The solvent was evaporated under vacuum and the residue partitioned between water (20 ml) and diethyl ether (20 ml). The aqueous layer was separated, washed with diethyl ether (2×20 ml) and evaporated under vacuum. The residue was treated with ethyl alcohol (10 ml) and evaporated to a clear gum which afforded a solid on addition of diethyl ether (20 ml) and scratching. The diethyl ether was decanted, the solid was treated with acetone and collected by filtration to afford 85 mg of N-[N-(2-Butyrothiolactone)amidomethyl] desipramine as a white solid.

Example 2

Preparation of N-[(Cysteine)amidomethyl]-desipramine

N-[N-(2-Butyrothiolactone)amidomethyl]-desipramine (9 mg, $1.8 \times 10^{-5}$ mol)was treated with dimethylformamide/water 70/30 v/v (724 µl) followed by 1 N potassium hydroxide solution (181 µl). The resulting solution was allowed to stand at room temperature for 10 minutes. The hydrolysis was immediately quenched by addition of 0.5 M potassium phosphate/0.1 M potassium borate buffer pH 7 which was made 1 N in hydrochloric acid (154 µl). The title compound in solution was used as is to react with thiol reactive groups, such as maleimides, alkyl halides or thiols, which are either free in solution or are coupled to proteins, polypeptides or labels.

Example 3

Preparation of N-[N-(2-Butyrothiolactone) amidomethyl]-nortriptylene

To a stirring solution of nortriptylene (300 mg, $1 \times 10^{-3}$ mol) and bromoacetyl-d,l-homocysteine thiolactone (Example 5) (262 mg, ($1.1 \times 10^{-3}$ mol) in anhydrous dimethylformamide (10 ml) was added freshly powdered anhydrous potassium carbonate (304 mg, $2.2 \times 10^{-3}$ mol). The mixture was stirred at room temperature for 25 hours. The solvent was evaporated under vacuum, the residue treated with ethyl acetate (10 ml) and the mixture filtered. The filtrate was washed with water (10 ml), dried over anhydrous magnesium sulfate and filtered. The filtrate was evaporated under vacuum to a foam which was triturated with diethyl ether (3×30 ml). The combined diethyl ether extracts were evaporated under vacuum. The residue was dissolved in ethyl acetate (10 ml) and acidified to pH 2 by dropwise addition of a 1 N solution of hydrogen chloride in diethyl ether to precipitate the crude product hydrochloride as a gummy solid. The product was triturated with ethyl acetate (3×30 ml). The combined ethyl acetate extracts were evaporated under vacuum and the residue partitioned between water (10 ml) and diethyl ether (10 ml). The aqueous layer was separated, washed with diethyl ether (2×10 ml) and evaporated under vacuum. The residue was treated with ethyl alcohol (10 ml) and evaporated to afford a white solid after addition of diethyl ether and acetone. The product was collected by filtration to afford 19 mg of N-[N-(2-Butyrothiolactone)amidomethyl]-nortriptylene as a white solid.

Example 4

Preparation of N-[(Cysteine)amidomethyl]-nortriptylene

N-[N-(2-Butyrothiolactone)amidomethyl]-nortriptylene (13.2 mg, $2.9 \times 10^{-5}$ mol) was treated with dimethylformamide/water 70/30 v/v (1.3 ml) followed by 1 N potassium hydroxide solution (328 µl). The resulting solution was allowed to stand at room temperature for 5 minutes. The hydrolysis was immediately quenched by addition of 0.5 M potassium phosphate/0.1 M potassium borate buffer pH 7 which was made 1 N in hydrochloric acid (300 µl). The title compound in solution was used as is to react with thiol reactive groups, such as maleimides, alkyl halides or thiols, which are either free in solution or are coupled to proteins, polypeptides or labels.

Example 5

Synthesis of 2-(2-Amino-4-Thiolbutanoic Acid Thiolactone)-Bromoacetamide (Bromoacetyl-HCTL)

Bromoacetic acid (1.0 g, $7.2 \times 10^{-3}$ mol), di-homocysteine thiolactone hydrochloride (1.1 g, $7.2 \times 10^{-3}$ mol) and pyridine (1.2 ml, $1.5 \times 10^{-2}$ mol) were dissolved in anhydrous dimethylformamide (36 ml) and then 1-(3-dimethylaminopropyl)-3-ethylcarbodiimide hydrochloride (1.52 g, $7.9 \times 10^{-3}$ mol) was added. The reaction was stirred at room temperature for 18 h. The solvents were removed in vacuo and ethanol (10 ml) was added to dissolve the residue and then the ethanol was removed in vacuo. Ethanol (10 ml) was again added to dissolve the residue and was removed in vacuo. Water (20 ml) was added to the oil and the aqueous solution was extracted 3 times with methylene chloride (45 ml). The combined organic extracts were dried over anhydrous magnesium sulfate. The solution was filtered and the solvent was removed in vacuo to give a clear oil. Diethyl ether (5 ml) was added and the resulting precipitate was collected and washed on a fritted funnel. The precipitate was dried in vacuo and 1.0 g of the title compound was recovered.

What is claimed is:

1. A compound of the formula:

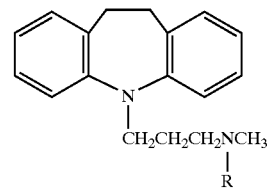

where R is a group comprising one of the following:

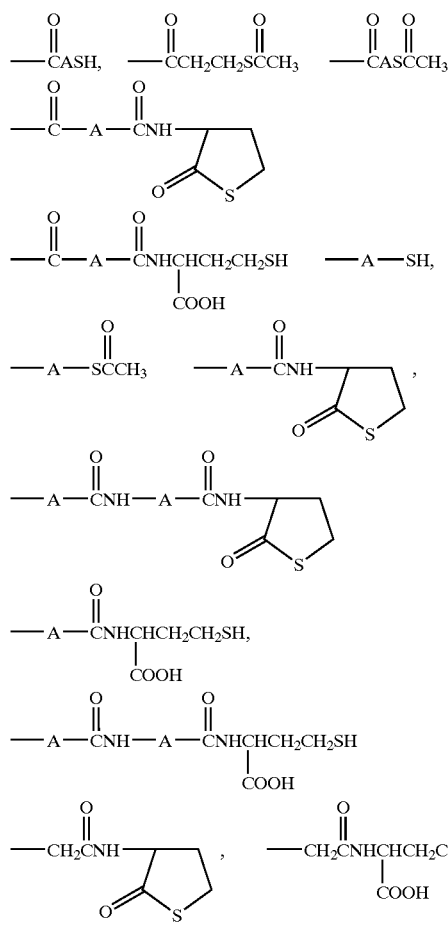

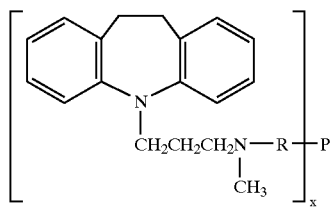

where A is a linking group from 1 to 20 carbons and from 0 to 10 heteroatoms (NH, O, S), either branched or straight chain.

2. Compounds of the formula:

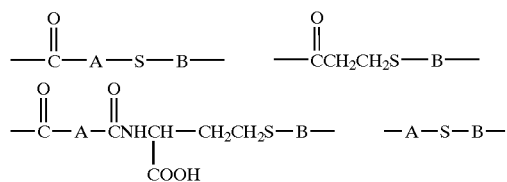

where P is an antigenic protein or polypeptide or a protein, polypeptide or label;
where x is at least one and not greater than 100;
where R is a linking group comprising one of the following:

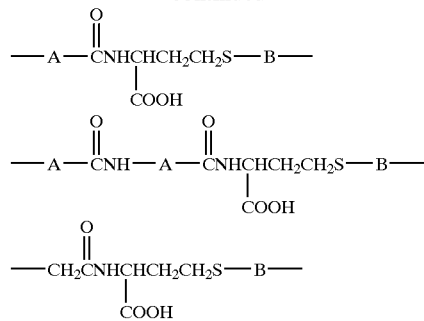

-continued

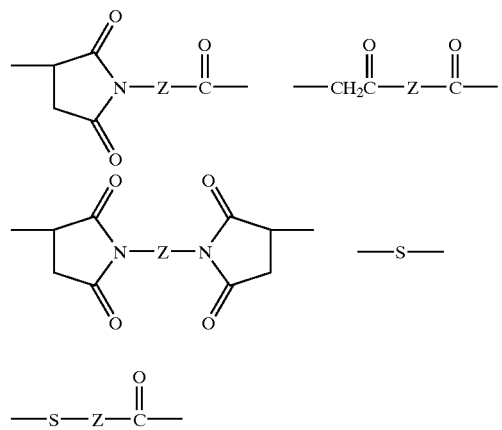

where A is a linking group of from 1 to 20 carbons and 0 to 10 heteroatoms (NH, O, S), either branched or straight chain;

where B is a linking group ultimately attached to a protein, polypeptide or label selected from the group consisting of:

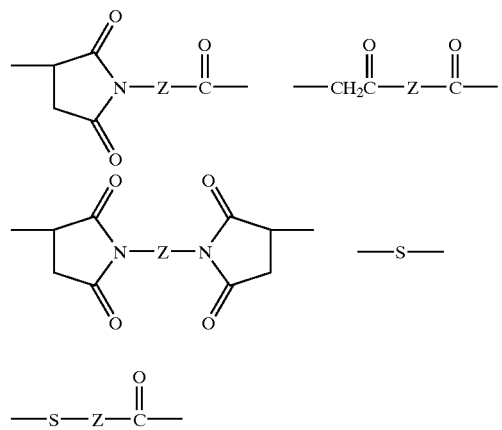

where Z is a linking group of from 1 to 20 carbons and 0 to 10 heteroatoms (NH, O, S), and may be branched or straight chain.

3. A method of preparing an antibody or antibody fragment comprising the step of:
using one of the compounds of claim 2 as an antigen to produce said antibody or antibody fragment.

4. The method of claim 3, wherein said antibody or antibody fragment comprises a binding domain which binds to an epitope on

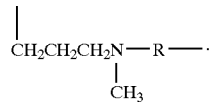

5. The method of claim 4 wherein said antibody or antibody fragment comprises a binding domain which binds to an epitope on

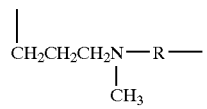

and an epitope on

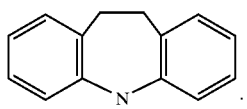

.

6. A compound of the formula:

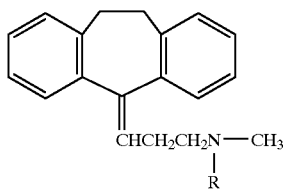

where R is a saturated or unsaturated group comprising one of the following:

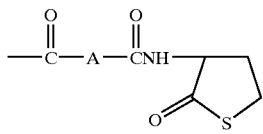

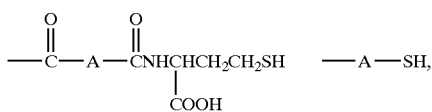

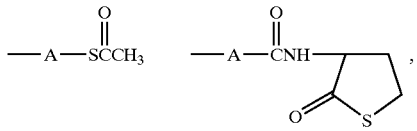

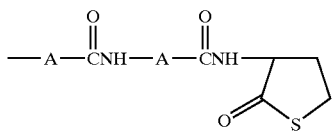

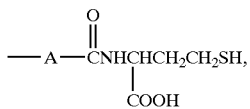

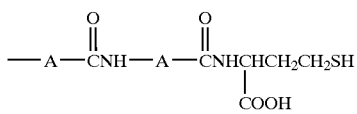

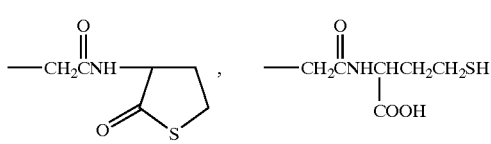

where A is a linking group of from 1 to 20 carbons and from 0 to 10 heteroatoms (NH, O, S), either branched or straight chain.

7. Compounds of the formula:

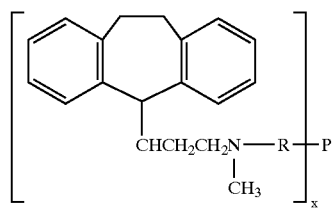

where P is an antigenic protein or polypeptide or protein, polypeptide or label;

where x is at least one and not greater than 100;

where R is a linking group consisting of one of the following:

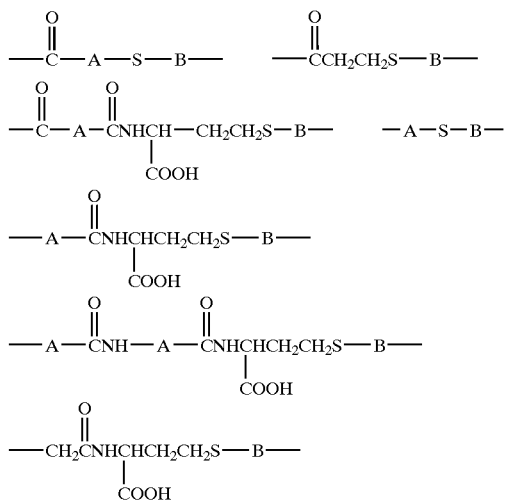

where A is a linking group of from 1 to 20 carbons and 0 to 10 heteroatoms (NH, O, S), either branched or straight chain;

where B is a linking group ultimately attached to a protein, polypeptide, or label selected from the group consisting of:

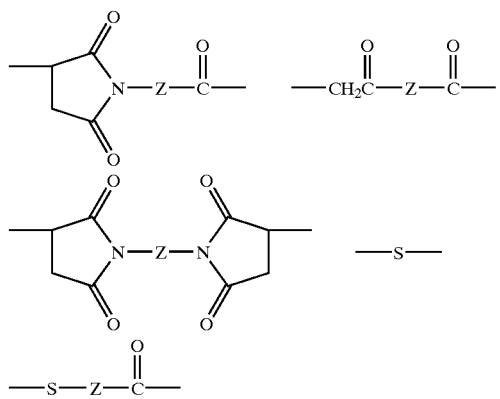

where Z is a linking group of from 1 to 20 carbons and 0 to 10 heteroatoms (NH, O, S) and may be branched or straight chain.

8. A method of preparing an antibody or antibody fragment comprising the step of:

using one of the compounds of claim 7 as an antigen to produce said antibody or antibody fragment.

9. The method of claim 8, wherein said antibody or antibody fragment rises a binding domain which binds to an epitope on

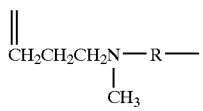

10. The method of claim 9 wherein said antibody or antibody fragment comprises a binding domain which binds to an epitope on

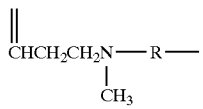

and an epitope on

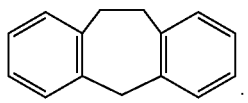

11. A compound of the formula:

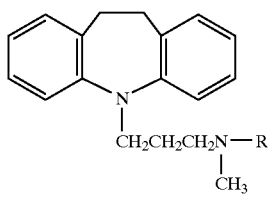

where R is selected from the group consisting of:

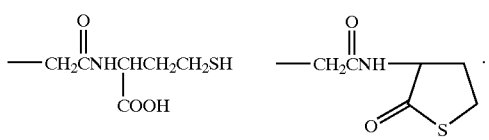

12. Compounds of the formula:

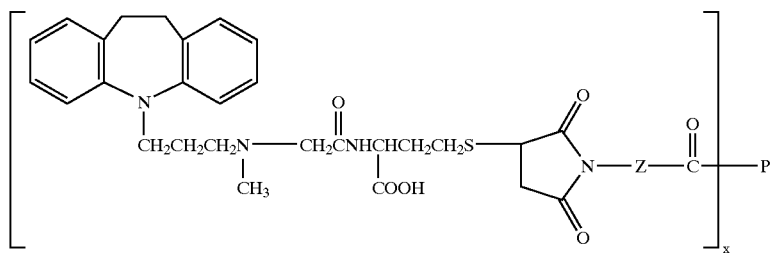

where P is an antigenic protein or polypeptide or a protein, polypeptide or label;

where x is at least one and not greater than 100;

where Z is a linking group of from 1 to 20 carbons and 0 to 10 heteroatoms (NH, O, S) and may be branched or straight chain.

13. A method of preparing an antibody or antibody fragment comprising the step of:

using one of the compounds of claim 12 as an antigen to produce said antibody or antibody fragment.

14. The method of claim 13 wherein said antibody or antibody fragment comprises a binding domain which binds to an epitope on

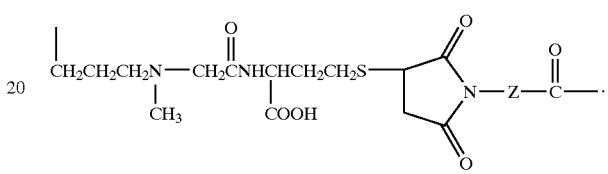

15. The method of claim 14 wherein said antibody or antibody fragment comprises a binding domain which binds to an epitope on

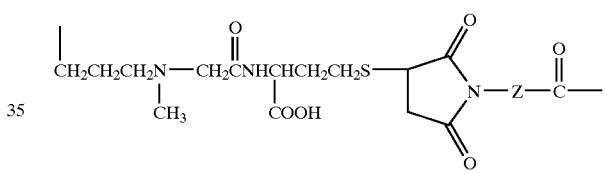

and an epitope on

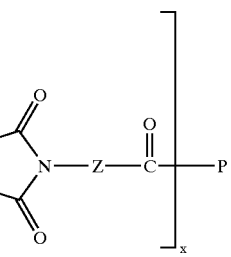

16. A compound of the formula:

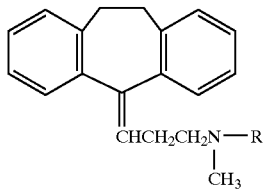

where R is a group comprising one of the following:

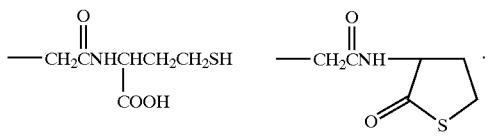

17. Compounds of the formula:

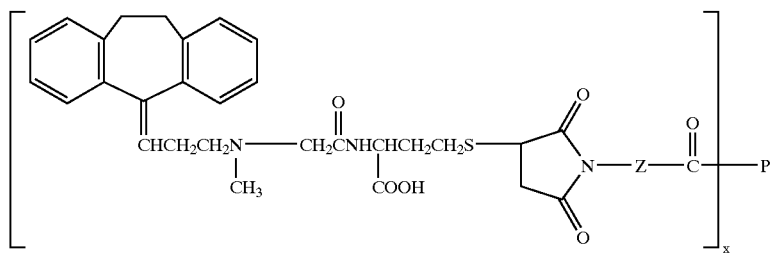

where P is an antigenic protein or polypeptide or a protein, polypeptide or label;

where x is at least one and not greater than 100;

where Z is a linking group of from 1 to 20 carbons and 0 to 10 heteroatoms (NH, O, S) and may be branched or straight chain.

18. A method of preparing an antibody or antibody fragment comprising the step of:

using one of the compounds of claim 17 as an antigen to produce said antibody or antibody fragment.

19. The method of claim 18 wherein said antibody or antibody fragment comprises a binding domain which binds to an epitope on

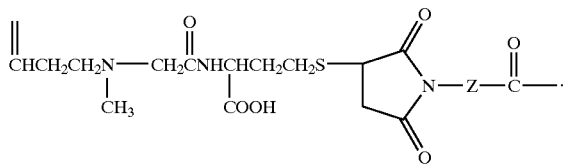

20. The method of claim 19 wherein said antibody or antibody fragment comprises a binding domain which binds to an epitope on

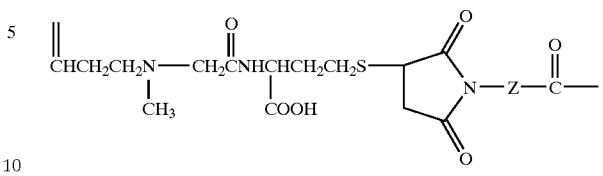

and an epitope on

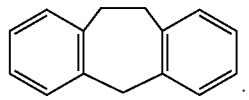

21. A compound of the formula:

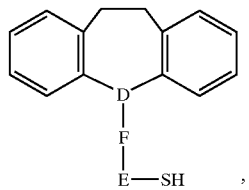

where D is C or N;
where F is a saturated or unsaturated, branched or straight chain comprising from 1 to 20 carbons and a nitrogen, and optionally, 0 to 10 heteroatoms (HN, O, S);
where E is a saturated or unsaturated linking group comprising from 1 to 20 carbons and 0 to 10 heteroatoms (HN, O, S) either branched or straight chain and is attached to the nitrogen group of F; and
where S is sulphur.

22. Compounds of the formula:

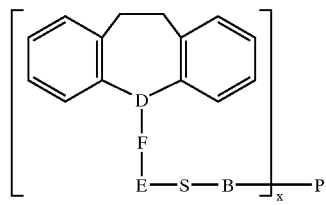

where x is at least one and not greater than 100;
where D is C or N;

where F is a saturated or unsaturated, branched or straight chain comprising from 1 to 20 carbons and a nitrogen, and optionally, 0 to 10 heteroatoms (HN, O, S);

where E is a saturated or unsaturated linking group comprising from 1 to 20 carbons and 0 to 10 heteroatoms (HN, O, S) either branched or straight chain and is attached to the nitrogen group of F;

where S is sulphur;

where B is selected from the group consisting of:

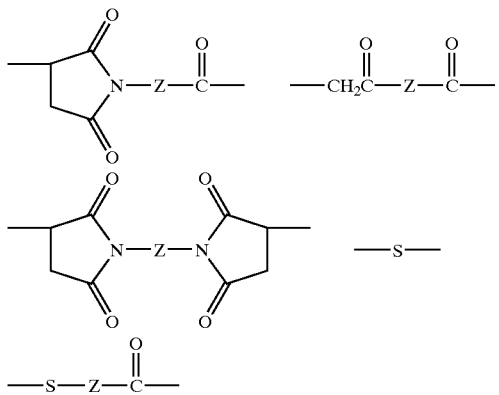

where Z is a linking group comprising from 1 to 20 carbons and 0 to 10 heteroatoms (NH, O, S) and may be branched or straight chain; and where P is an antigenic protein or polypeptide or a protein, polypeptide or label.

23. A method of preparing an antibody or antibody fragment comprising the step of:

using one of the compounds of claim 22 as an antigen to produce said antibody or antibody fragment.

24. The method of claim 23 wherein said antibody or antibody fragment comprises a binding domain which binds to an epitope on F, E, S, or B or some combination thereof.

25. The method of claim 24, wherein said antibody or antibody fragment comprises a binding domain which binds to an epitope on F, E, S, or B or some combination thereof and an epitope on

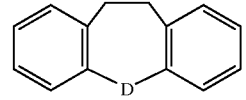

where D is C or N.

* * * * *

UNITED STATES PATENT AND TRADEMARK OFFICE
CERTIFICATE OF CORRECTION

PATENT NO. : 6,803,040 B1 Page 1 of 1
APPLICATION NO. : 08/517949
DATED : October 12, 2004
INVENTOR(S) : Buechler et al.

It is certified that error appears in the above-identified patent and that said Letters Patent is hereby corrected as shown below:

In the claims:

Claim 7, Column 20, Lines 63 and 64, replace "0 to heteroatoms" with -- 0 to 10 heteroatoms --

Claim 9, Column 21, Line 4, replace "rises" with -- comprises --

Signed and Sealed this

Twenty-fifth Day of July, 2006

JON W. DUDAS
*Director of the United States Patent and Trademark Office*